(12) United States Patent
Kruger (10) Patent No.: US 7,774,042 B2
(45) Date of Patent: *Aug. 10, 2010

(54) TISSUE SCANNER (75) Inventor: Robert A. Kruger, Indianapolis, IN (US)

(73) Assignee: Senco Brands, Inc., Cincinnati, OH (US)

( * ) Notice: Subject to any disclaimer, the term of this patent is extended or adjusted under 35 U.S.C. 154(b) by 1203 days.

This patent is subject to a terminal disclaimer.

(21) Appl. No.: 10/672,137

(22) Filed: Sep. 26, 2003

(65) Prior Publication Data

US 2004/0127783 A1    Jul. 1, 2004

Related U.S. Application Data

(60) Provisional application No. 60/414,000, filed on Sep. 26, 2002.

(51) Int. Cl.
*A61B 5/05* (2006.01)
(52) U.S. Cl. .................. 600/407; 600/437; 600/473; 600/476; 600/408; 600/409; 600/424; 600/425; 600/430; 600/436; 374/117
(58) Field of Classification Search ......... 600/407–409, 600/437–461, 473, 476; 374/117
See application file for complete search history.

(56) References Cited

U.S. PATENT DOCUMENTS

| 4,407,008 | A  | * | 9/1983 | Schmidt et al. ............... 348/79 |
| 5,339,282 | A  | * | 8/1994 | Kuhn et al. ..................... 367/7 |
| 6,216,540 | B1 | * | 4/2001 | Nelson et al. ................. 73/633 |
| 6,567,688 | B1 | * | 5/2003 | Wang ......................... 600/430 |

* cited by examiner

*Primary Examiner*—Brian Casler
*Assistant Examiner*—John F Ramirez
(74) *Attorney, Agent, or Firm*—Wood, Herron & Evans, LLP (57) ABSTRACT

A three-dimensional thermoacoustic imaging system uses dye markers. Thermoacoustic signals are produced by the dye markers when light from an external source is absorbed by the dye. Thermoacoustic images with and without dye stimulation may be generated using excitation frequencies both inside and outside the frequency band of fluorescence of the dye marker, and these may be combined, and/or combined with conventional ultrasound images for image enhancement. An apparatus for carrying out this method on mice, uses a commercially available array of transducers positioned opposite to the body of the mouse, which is immersed in a coupling media. A source of illumination such as a laser directs light to the mouse through the coupling media, and resulting acoustic waves are captured by the array and reconstructed to form an image.

13 Claims, 9 Drawing Sheets

Absorption

TISSUE SCANNER

This application claims priority from U.S. Provisional patent application No. 60/414,000, filed Sep. 26, 2002, and application Ser. No. 09/884,766 filed Jun. 19, 2001, now U.S. Pat. No. 6,490,470, a divisional of which was filed Nov. 15, 2002, as application Ser. No. 10/295,468, which issued as U.S. Pat. No. 6,633,774 on Oct. 15, 2003. This application is related to application Ser. No. 09/243,004 filed Feb. 2, 1999, entitled THERMOACOUSTIC COMPUTED TOMOGRAPHY SCANNER, now U.S. Pat. No. 6,216,025, which is a divisional application of Ser. No. 09/076,385 filed May 12, 1998, now U.S. Pat. No. 6,104,942, and application Ser. No. 09/076,968 filed May 13, 1998, now U.S. Pat. No. 6,102,857, which is a divisional of Patent Cooperation Treaty application designating the Ser. No. 97/17832, filed Oct. 1, 1997, which is a continuation of application Ser. No. 08/719,736, filed Oct. 4, 1996, now U.S. Pat. No. 5,713,356, issued Feb. 3, 1998, all of the foregoing being filed in the name of the same inventor as the present application and assigned to the same assignee as the present application, and all of the foregoing hereby incorporated by reference into this application.

FIELD OF THE INVENTION

The present invention relates to imaging properties of tissue using optical and photo-acoustic techniques.

BACKGROUND OF THE INVENTION

It is well established that different biologic tissues display significantly different interactions with electromagnetic radiation from the visible and infrared into the microwave region of the electromagnetic spectrum. The photoacoustic effect was first described in 1881 by Alexander Graham Bell and others, who studied the acoustic signals that were produced whenever a gas in an enclosed cell is illuminated with a periodically modulated light source. When the light source is modulated at an audio frequency, the periodic heating and cooling of the gas sample produced an acoustic signal in the audible range that could be detected with a microphone. Since that time, the photoacoustic effect has been studied extensively and used mainly for spectroscopic analysis of gases, liquid and solid samples.

It was first suggested that photoacoustics, also known as thermoacoustics, could be used to interrogate living tissue in 1981, but no subsequent imaging techniques were developed. In Bowen U.S. Pat. No. 4,385,634, ultrasonic signals are induced in soft tissue whenever pulsed radiation is absorbed within the tissue; these ultrasonic signals are detected by a transducer placed outside the body. Bowen derives a relationship (Bowen's equation 21) between the pressure signals $p(z,t)$ induced by the photoacoustic interaction and the first time derivative of a heating functions, $S(z,t)$, that represents the local heating produced by radiation absorption. Bowen teaches that the distance between a site of radiation absorption within soft tissue is related to the time delay between the time when the radiation was absorbed and when the acoustic wave was detected.

The above-referenced U.S. patents and applications filed by the present inventor, detail a diagnostic imaging technique in which pulses of electromagnetic radiation are used to excite a relatively large volume of tissue and stimulate acoustic energy. Typically, a large number of such pulses (e.g., 100 to 100,000), spaced at a repetition interval, are generated to stimulate the tissue. The above-referenced U.S. Pat. No. 5,713,356 discloses methods for measuring the relative time delays of the acoustic waves generated by a sequence of such pulses, and for converting these time delays into a diagnostic image.

The use of small animals, and mice in particular, has become increasing prevalent in laboratory research. Mice, and particularly transgenic mice, have been useful in locating and eliminating causes and treatments for disease. Currently 30 million mice are used in medical research annually. In these applications, it is necessary to examine mice efficiently, in vivo, to detect the condition of the mice in order to assess progress of a study.

Optical fluorescence imaging has frequently been used in imaging transgenic mice. Optical fluorescence imaging allows researches to detect proteins, antibodies and genetic markers in vivo that have been labeled with fluorescing dyes. However, the deleterious effects of optical scattering compromises fluorescence imaging in intact animals, and limits spatial resolution increasingly with the depth of the site of markers within soft tissue.

SUMMARY OF THE INVENTION

In one aspect, the invention features a three-dimensional thermoacoustic imaging system using dye markers. The thermoacoustic method operates not by detecting fluorescence of the dye markers, but rather the thermoacoustic signals that are produced by the dye markers when light from an external source is absorbed by the dye.

While applicable to a variety of imaging environments, including imaging of human tissue in vivo, the method has been developed in the context of imaging mice used in laboratory experiments. The thickness of the typical athymic mouse is less than 20 mm; therefore, to create and detect thermoacoustic absorption of light in a mouse, the maximum penetration of light into the mouse tissue would not need to exceed 10 mm. In humans and other large animals, imaging using this method could be performed anywhere near the surface of the tissue.

An apparatus for carrying out the method of the present invention in imaging mice comprises an array of transducers positioned opposite to the body of the mouse, which is immersed in a coupling media. A source of illumination such as a laser directs light to the mouse through the coupling media to cause thermoacoustic absorption of light by the tissues of the mouse. The resulting acoustic waves are captured by the array and reconstructed to form an image of the internal tissues of the mouse reflecting the locations of the labeling dye.

In the described specific embodiment, the array is a flat array of transducers, such as are commercially available, positioned vertically opposite to the mouse.

Thermoacoustic imaging using fluorescent dye markers may be used in combination with thermoacoustic imaging, and/or conventional ultrasound imaging, to produce overlaid enhanced images. Specifically, excitation frequencies both inside and outside the frequency band of fluorescence of the dye marker may be used to develop thermoacoustic images using and independent of the dye marker fluorescence.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF SPECIFIC EMBODIMENTS

Figure 1:
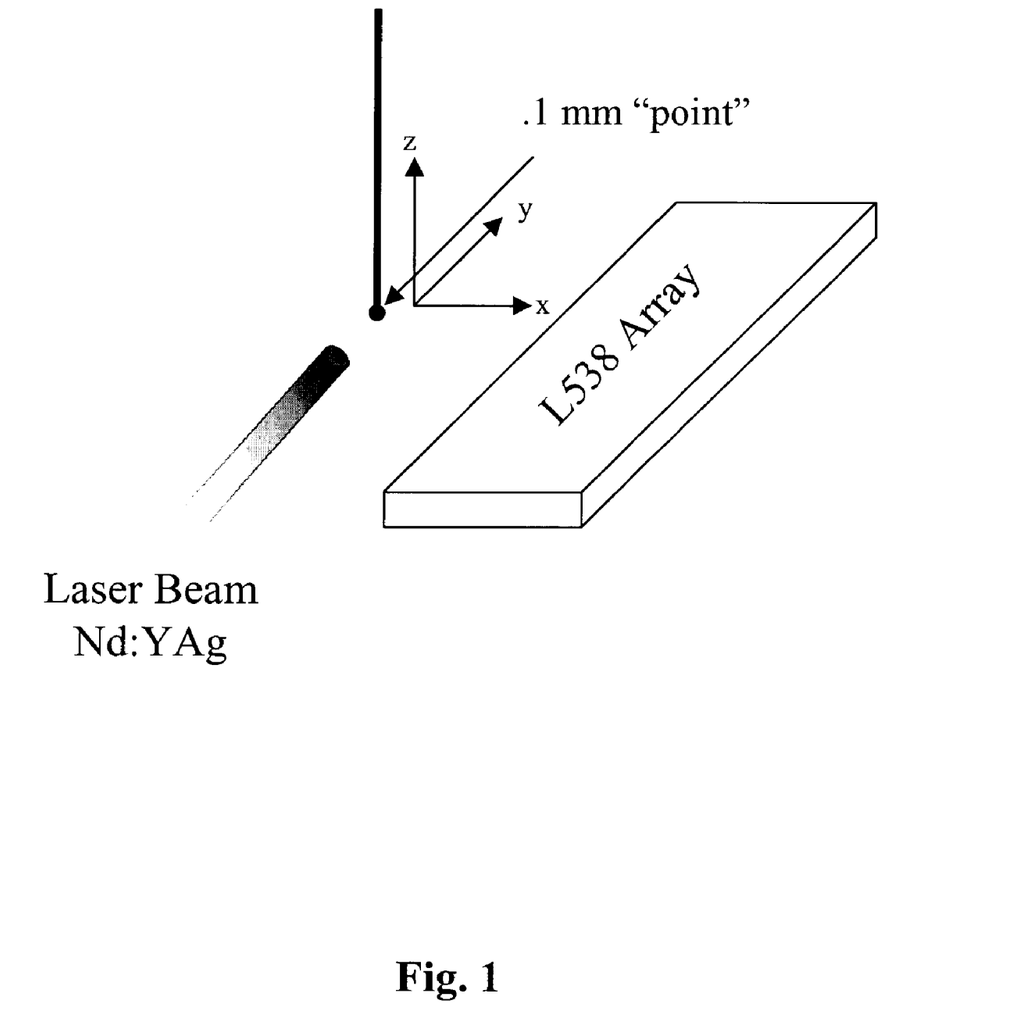
FIG. 1 is a perspective view of an experimental apparatus for evaluating the use of a linear array of transducers for imaging in accordance with principles of the present invention.

FIG. 1 illustrates a commercial, linear array 8 arranged for testing as a photoacoustic detector (specifically, Model No. L538, available from Acuson, Mountain View, Calif.). This array comprises 128 elements spanning 38 mm. The elements have a nominal central frequency of 5 MHz, and are spaced 0.3 mm apart. Each element is nominally 6-mm high, with a thin acoustic lens that produced a geometric focus approximately 15 mm in front of the array.

The slice-width profile of this array was measured normal to the imaging plane, from the axial response of the array to a photoacoustic "point" source 9, as illustrated in FIG. 1. The thermoacoustic "point" was fabricated by painting a small "dot" of black paint on the end of a 0.10-mm diameter, polyethylene thread. The thread was mounted on a two-axis positioner and pulsed with light from a Nd:YAg laser, which produced an approximately 6 ns pulse of 1064 nm infrared radiation. The position of the point source was slowly varied with a 2-axis positioner (in x,z on the illustrated axes). A single element of the array 8 was coupled to a low-noise preamplifier (40 dB, 10 MHz bandwidth), and fed to a digitizing oscilloscope (Model No. TDS 620B, available from Tektronix, Beaverton, Oreg.). The point source was positioned in front of this element. Data acquisition was triggered with the Q-switch sync from the laser.

The point source was placed 10 mm in front of the array, and adjusted in the z-axis until the peak-to-peak thermoacoustic signal was a maximum. That vertical point was assumed to be the imaging (central) plane of the linear array. The peak-to-peak thermoacoustic signal was then recorded as a function of the axial (x-axis) position.

The point source was positioned at x=20 mm, near the center of the peak-response zone (focal zone), which extended from approximately 10-30 mm in front of the array. The peak-to-peak thermoacoustic signal, plotted as a function of the z-position, was interpreted as the slice-thickness profile.

Figure 2:
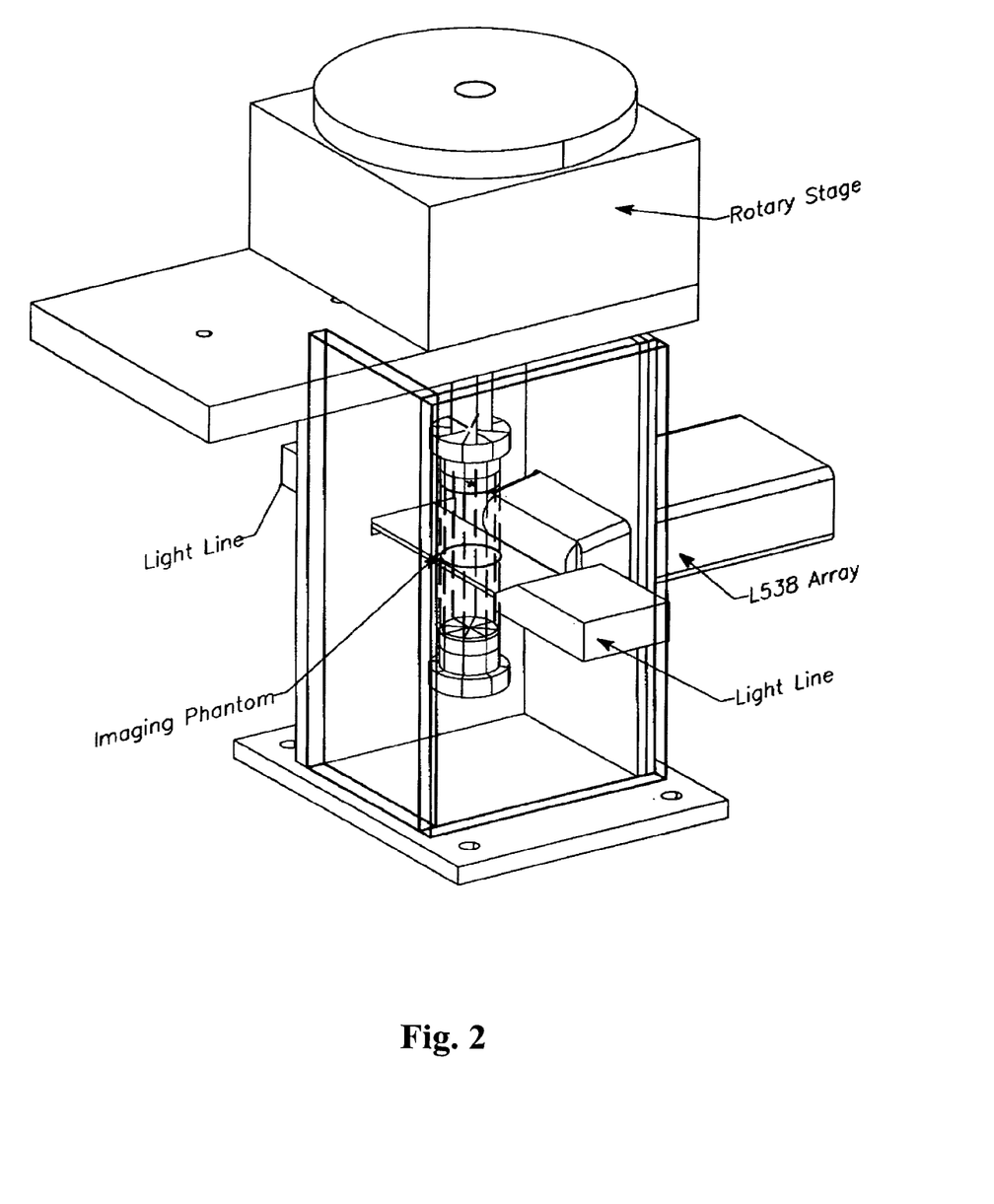
FIG. 2 is a perspective view of a thermoacoustic tissue scanner suitable for in vivo imaging of small animals or small tissue samples.

A photoacoustic apparatus 10, suitable for in vivo imaging of small animals and small tissue samples, is illustrated in FIG. 2. The specimen to be evaluated is contained in a water-filled, rectangular imaging tank 12 fabricated from clear plastic. The L538 array 8 was embedded in one side of the tank. During the test imaging described below, phantoms to be imaged were positioned within an approximately 20-mm diameter, cylindrical volume constructed of 0.004" thick FEP plastic. This plastic "cylinder" was attached to mandrels 14 top and bottom. The top mandrel was affixed to a rotary stage 17 that could be rotated through 360 degrees. Light from a Nd:YAg laser (not shown) was fed to a fiber-optic light guide, which was split into two linear sources (1"×0.070" "light lines" 16), and illuminated the imaging volume from opposing directions as illustrated in FIG. 2. The light lines were positioned vertically to lie near the imaging plane of the transducer array. The light output from each light line was ~5 mJ/pulse. The laser was pulsed at 10 Hz during data acquisition.

The L538 array was connected to a 128-channel digital acquisition system (DAS). The DAS had a 10 MHz analog bandwidth. All 128 channels were digitized to 10-bit precision at a sampling rate of 20 MHz for 1024 time samples. The DAS captured photoacoustic data at 1 or 16 angles spanning 360 degrees. Signal averaging (16 pulses) was performed at each angle.

Photoacoustic images were reconstructed using a filtered-backprojection algorithm described in the above-referenced U.S. patents. To implement this algorithm, the first derivative of the recorded photoacoustic signals for each transducer element and each angle were back-projected over circular arcs centered at each transducer element's location. The radii of the arcs were proportional to the delay times between the laser's Q-switch trigger and the recorded photoacoustic signals, where the constant of proportionality was the temperature-dependent velocity of sound in water. Two-dimensional images were reconstructed on a 256×256 grid of 0.1-mm pixels.

For ultrasound image formation, the output of the L538 array was connected to an Acuson 128 XP ultrasound imaging system, which was operated according to manufacturer's instructions.

To measure the 2-D impulse response (spatial resolution) of the PCT system, the point source was suspended from the top mandrel 14 of the phantom holder (FIG. 2) approximately 20 mm in front of the array. The vertical position of the point source was adjusted to lie within the central plane of the transducer array.

To test the ability of the system to image an optically absorbing target through turbid media, a tissue-mimicking phantom was fabricated. The phantom is designed to mimic the optical and acoustic properties of mice. Suitable phantoms are comprised of Agar gels doped with various concentrations of 20% Liposyn, India Ink, glass micro-spheres, and graphite powder. Liposyn is a fatty emulsion, similar to Intralipid, which may be used to emulate the optical scattering properties of soft tissue. India Ink will be used to emulate the optical absorption properties of soft tissue. Glass microspheres (83 :m mean diameter) will be used to mimic the acoustic scattering; and graphite powder will be used to mimic acoustic attenuation. These Agar-based phantoms may be molded in plastic tubes of the size that eventually will be used to immobilize mice.

There are two parameters that can be used to characterize the optical properties of soft tissue—its effective scattering coefficient $\mu_s'$, and its linear absorption coefficient $\mu_a$. The effective attenuation coefficient $\mu_{eff}$ is related to these two parameters according to: $\mu_{eff} \approx \sqrt{3\mu_a(\mu_a+\mu_s)}$, under the assumption that $\mu_s' >> \mu_a$, which is generally true in the near infrared. The optical properties of some rat tissues, measured at 1064 nm, are tabulated in Table 1. These data provide a target range of values that we would like to mimic in our phantom construction.

| Rat Tissue | $\mu_a$(cm$^{-1}$) | $\mu_s'$(cm$^{-1}$) | $\mu_{eff}$(cm$^{-1}$) |
|---|---|---|---|
| Skin | .23 | 9.1 | 2.5 |
| Liver | 1.3 | 8.25 | 6.1 |

The scattering properties of Intralipid 10% at 1064 nm have been documented. We assume that the optical scattering of Liposyn 20% is twice that of Intralipid 10%, since its lipid constituents are identical to those of Intralipid 10%, but at twice the concentration. Consequently, we will assume the effective scattering coefficient of Liposyn 20% is related to its % concentration according to:

$$\mu_s'(cm^{-1}) \approx 1.31\% \text{ (Liposyn 20\%)}. \quad (1)$$

The absorption coefficient of India Ink has been measured as:

$$\mu_a'(cm^{-1}) \approx 27\% \text{ (Indian Ink)}. \quad (2)$$

We assume the absorption coefficient of pure water is 0.15 cm$^{-1}$ at 1064 nm. Assuming these optical properties of water, Liposyn 20% and India Ink, we can produce a range of scattering and absorption coefficients spanning the range tabulated in Table I by constructing our phantoms using the following constituents: 5-10% Liposyn 20%, 0-0.03% India Ink, 90-95% deionized water.

A 4 g per liter concentration of glass micro-spheres (A2429 glass beds from Potters Industries, 83 mm mean diameter), suspended in Agar, simulates the levels of acoustic scatter encountered in soft tissue. Additionally, we will add 0.05-0.10 g/cm$^3$ of graphite powder to the same Agar phantom to produce ~0.5 dB/cm/MHz acoustic attenuation.

A strategy for producing phantoms that mimic both the optical and acoustic properties of soft tissue is to combine appropriate concentrations of Liposyn 20%, India Ink and water into a stock solution, used in place of water to construct our Agar gels. Micro-spheres and graphite powder may be added to a heated Agar solution prior to cooling the gel in cylindrical molds.

For the images discussed below, a phantom was constructed using 4% Agar, India Ink and Liposyn-20%. A 6-mm diameter cylinder of 4% Agar doped with 0.01% India Ink produced an absorption coefficient of 0.42 cm$^{-1}$ at 1064 nm. Optical scattering was negligible. This absorbing phantom was placed within the 20-mm diameter phantom holder, with the rest of the phantom holder filled with 4% Agar doped with 8% Liposyn-20%, which produced an absorption coefficient of $\mu_a$~0.15 cm$^{-1}$ (due almost entirely to water), and a reduced scattering coefficient of $\mu_s'$~10 cm$^{-1}$. The Agar+Liposyn combination also produced a phantom with reasonable acoustic scattering properties for ultrasound image formation.

Figure 3:
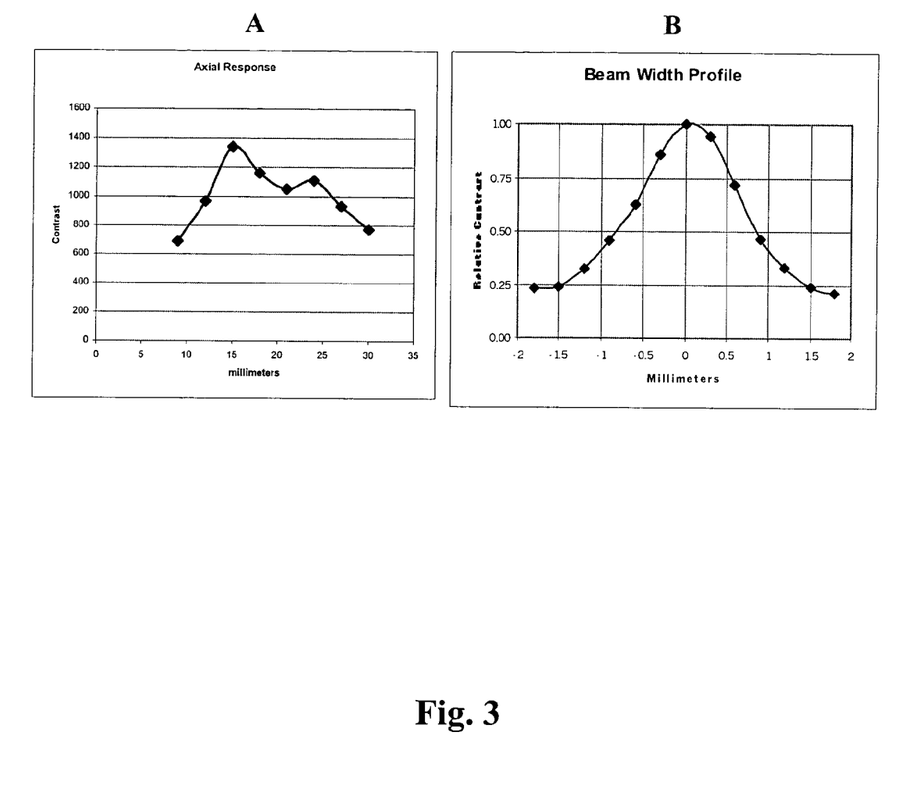
FIGS. 3A and 3B are plots of the photoacoustic response of the linear array in the scanner of FIG. 2.

FIG. 3A plots the peak-to-peak photoacoustic response to the above-described point source as a function of axial position in front of the L538 array. FIG. 3B shows the slice width profile measured at an axial position 20 mm in front of the array using the same point source. The FWHM of the slice width profile measured 1.5 mm.

Figure 4:
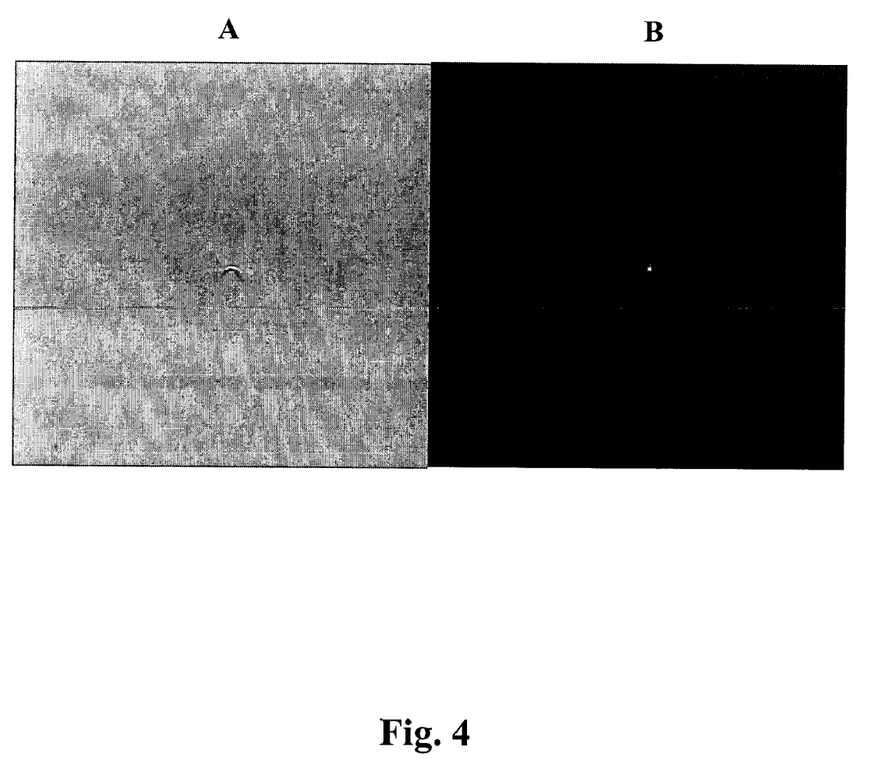
FIGS. 4A and 4B are 256×256 pixel images of the point source reconstructed from data at 1 and 16 angles, respectively.

FIGS. 4A and 4B show photoacoustic images reconstructed according to the methods of the above-referenced U.S. patents, of the 0.1-mm point source reconstructed from data at 1 and 16 angles, respectively. The images are 256×256 elements and span 25.6 mm on a side. These images are interpreted to represent the 2-D point spread responses (PSF) of the PCT system convolved with the 0.1-mm width of the point source for 1- and 16-angle acquisitions.

Figure 5:
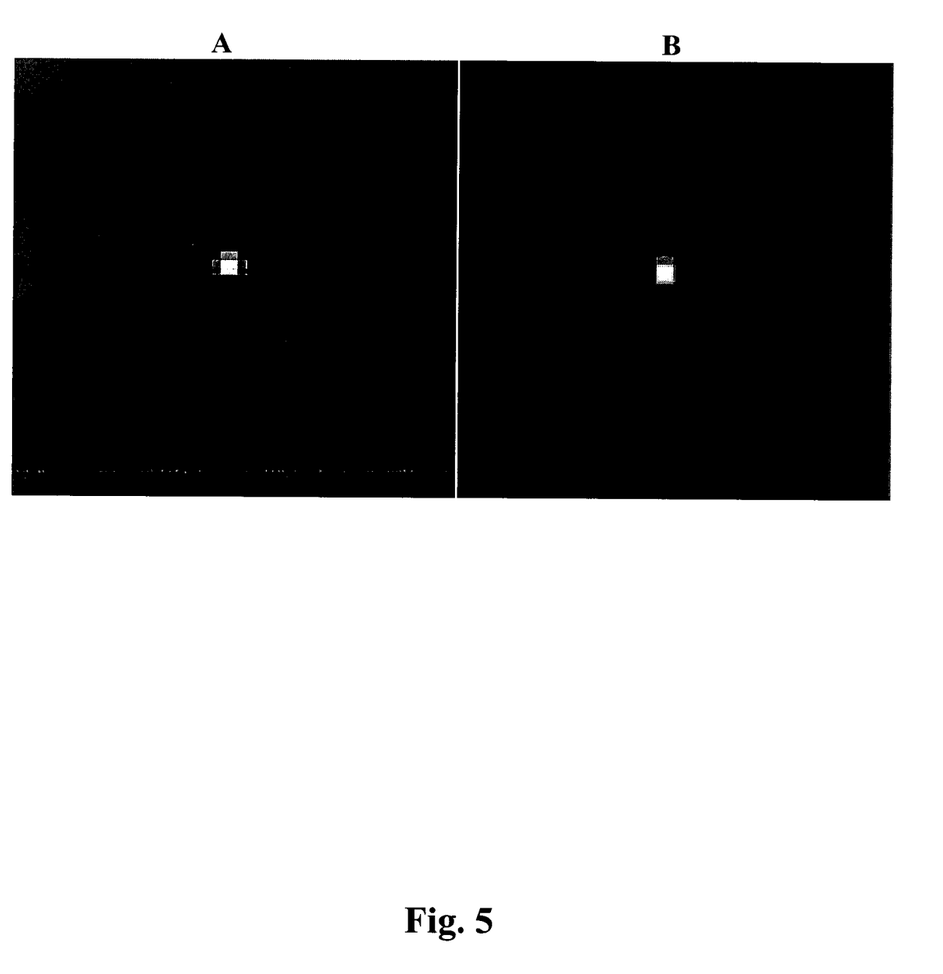
FIG. 5A is an expanded views of the central portion of FIG. 4B.
FIG. 5B is a Gaussian curve fit to this data using nonlinear least squares optimization.

FIG. 5A shows an expanded view of the central portion of FIG. 4B. A 2-D Gaussian was fit to these data using nonlinear least squares. The resultant Gaussian fit is pictured in FIG. 5B. The standard deviation of this Gaussian is 90 microns, corresponding to a FWHM of 180 microns.

Figure 6:
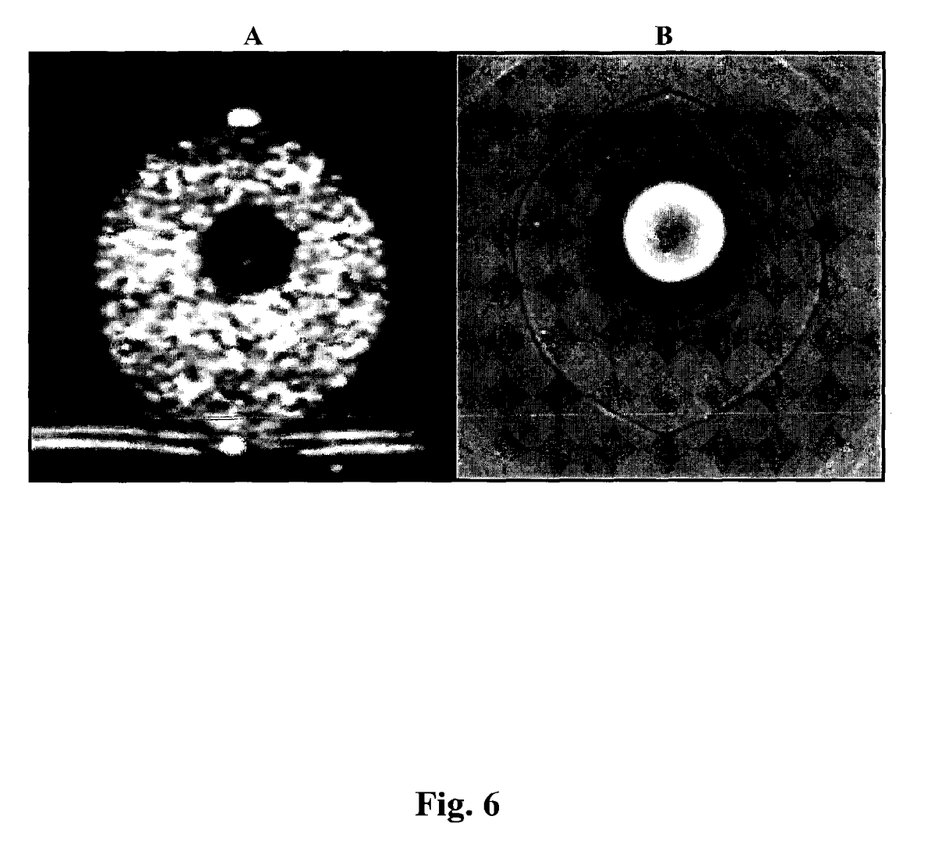
FIGS. 6A and 6B compare respective ultrasound and photoacoustic images of the phantom.

The ultrasound and PCT images of the tissue-mimicking phantom are compared in FIGS. 6A and 6B.

As shown, based on the measurement of the axial response of the transducer array to a photoacoustic point source, there was a relatively uniform region of photoacoustic response between 10-30 mm in front of the linear array, which was used for imaging. To obtain data from multiple angles, the phantom and array were rotated relative to each other about a point 20 mm in front of this array. Using the apparatus of FIG. 2, the tissue/phantom was rotated rather than the detector array, however, rotation of array about the tissue/phantom would have generated equivalent results.

The spatial resolution of this imaging system may be estimated by deconvolving the effect of the finite size of the point source from the Gaussian fit to its image (FIG. 5B). Accordingly, the FWHM of the PSF of the system was estimated as: $PSF_{FWHM} = \sqrt{180^2 - 100^2} = 150$ microns. This spatial resolution corresponds to $\lambda/2$ of the central frequency (5 MHz) of the L538 array, consistent with theory.

The presence of Liposyn in the outer region of the tissue-mimicking cylinder produced noticeable speckle in the ultrasound image, seen in FIG. 6A, and little speckle within the 6-mm cylinder of 4% Agar+0.01 India Ink, which contained no acoustic (or optical) scatterer. In the PCT image, there is no noticeable acoustic speckle or photoacoustic contrast within the outer region of the larger cylinder, whose absorption coefficient was virtually the same as the surrounding water. Within the smaller cylinder there is significant differential photoacoustic contrast between the inner and outer cylinders, corresponding to the increased absorption produced by the 0.01% India Ink. The spatial resolution of the PCT image was clearly superior to the ultrasound image using the same detector array. This is because the bandwidth of the detector, operated in receive-only mode, is better than its pulse-receive bandwidth of the same array. The PCT image also was formed directly from the RF signal without the need for envelope detection, which compromises spatial resolution.

Imaging small animals, e.g., mice, both photoacoustically and ultrasonically, and be used to perform in vivo optical spectroscopy to study endogenous or exogenous chromophore distributions in small animals, and to quantify optical-dye-labeled molecular species.

Figure 7:
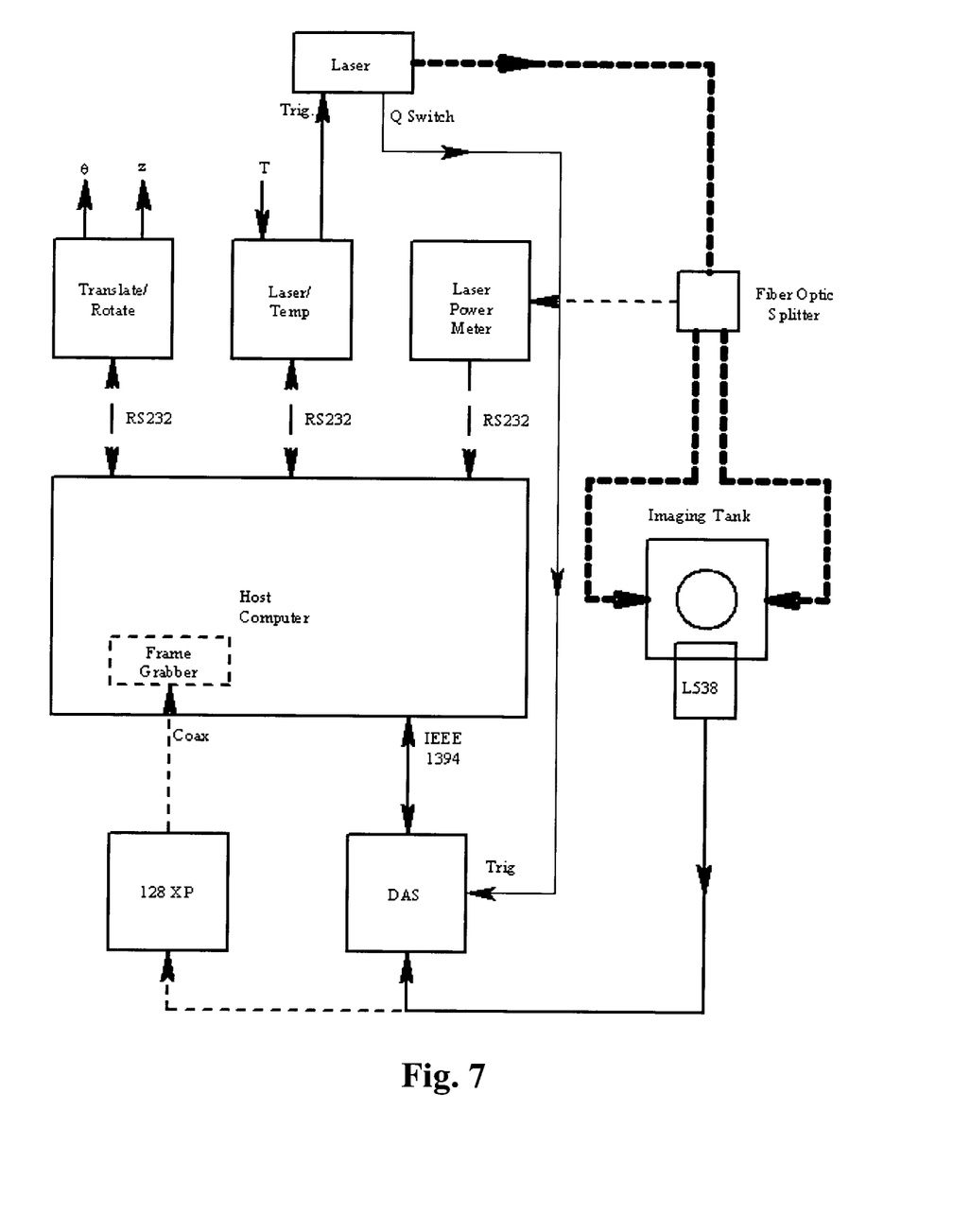
FIG. 7 is a block diagram of a ultrasound/thermoacoustic imaging system in accordance with principles of the present invention.

FIG. 7 illustrates a hardware and software system for acquiring conventional ultrasound, compound ultrasound, and thermoacoustic images. It consists of a host computer 20, which is interfaced to electronics 22 for controlling the translation (Z) and rotation (2) stages of the cylindrical mouse holder within the imaging tank 10, triggering the laser 24, monitoring water temperature (T) via sensor electronics 27 and the output laser power via sensor electronics 28; and collecting image data from the L538 array 8 through either the Acuson 128 XP 310 or the DAS 32.

Software in the host computer will control the rotation and translation of the mouse immobilizer vai electronics 22, the number of angles to be acquired, the number of integrations to be collected at each angle, and the total scan angle for each axial image to be acquired. The water temperature and output laser power will be monitored during image acquisition, which in turn will be used for image reconstruction.

One way in which a combined US and TCT scanner can be used, is to use the US capability to localize a site of tissue anomaly, e.g., a breast "mass." Once localized, a TCT image can be acquired of the same mass to determine its optical (or radio wave, or microwave) absorptive properties. Such information can aid in characterizing the nature of the anomaly in question. Additionally, dye-labeled proteins, monoclonal antibodies, or other biochemical markers, which target cancer or other diseases, can be injected into a patient. After some time delay, TCT can be used to determine if the dye has accumulated in the suspicious mass or tissue.

Figure 8:
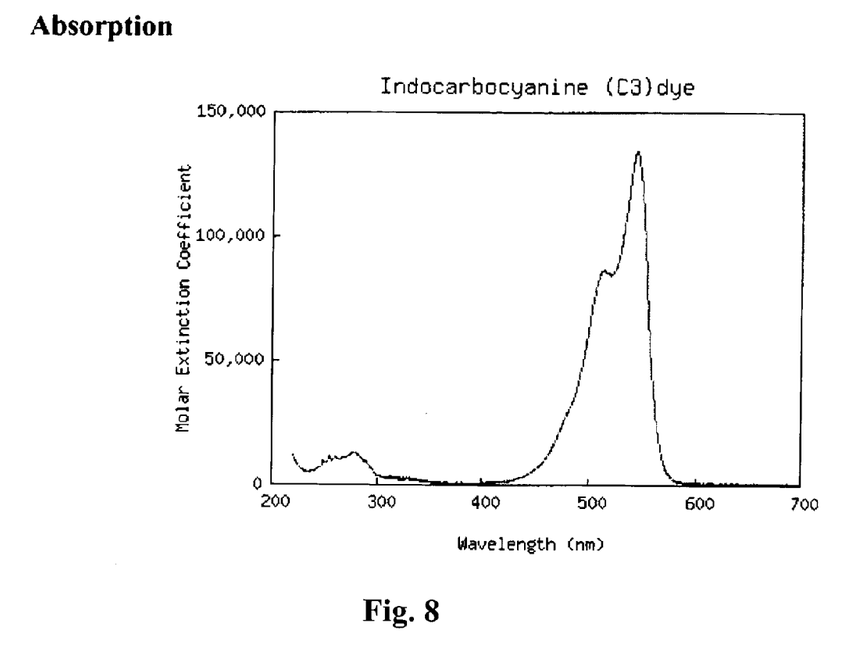
FIG. 8 illustrates the fluorescence response band of Indocarbocanine dye.

In cases where dye markers are used, the laser wavelength would be chosen to correspond to the wavelength where peak absorption of the dye occurs. For example, a laser that operated at 548 nm would be used with the Cy3 dye, whose absorption properties are shown in FIG. 8. Additionally, two TCT images may be formed using two different wavelengths, one near the dye's peak absorption, one slightly higher where absorption by the dye is low (550 and 600 nm for the Cy3 dye). Since these two wavelengths are close together, the absorption due to endogenous tissue will not vary much between the two images. However, only the image taken at 550 nm will display absorption due to the Cy3 dye. Subtracting the two images on a point by point basis, would isolate the dye absorption from that of endogenous chromophores, producing a map of Cy3 dye distribution in the tissue. This method can be extended and applied to multiple dyes simultaneously by using additional wavelengths.

Figure 9:
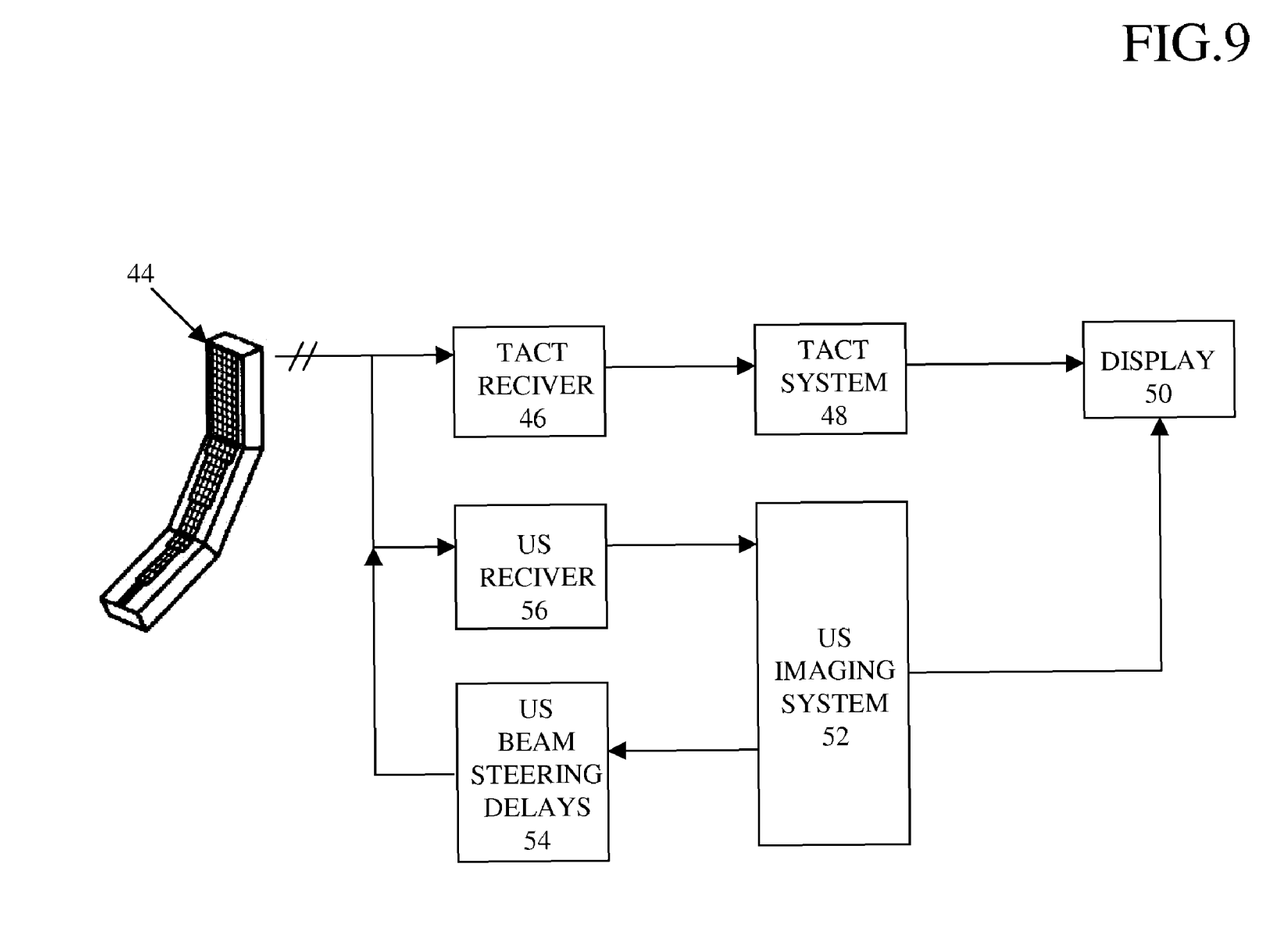
FIG. 9 is an illustration of the electronic circuitry used in a combination TACT and ultrasound imaging system using the scanner of FIG. 2.

Referring now to FIG. 9, the use of detector array 44 in TACT imaging as well as ultrasonic imaging can be explained. A further advantage of detector array 44 is that it provides an array of adjacent acoustic sensors that may also be used in a conventional ultrasound process for ultrasound imaging of the breast tissue in conjunction with or in addition to thermoacoustic imaging. Specifically, the acoustic sensors in detector array 44 are coupled to a TACT receiver 46 and to a TACT processing system 48 for producing TACT images using acoustic signals detected by the detector array 44. Details of this process are described in the above-referenced U.S. Pat. No. 5,713,356, and are not repeated here. The resulting TACT-generated image may be displayed on a display for diagnostic purposes. Simultaneously, or as a separate imaging modality, the sensors on array 44 may be used for conventional ultrasound imaging of the subject tissue. Specifically, for this application, an ultrasound beam steering delay circuit 54 is controlled by an ultrasound imaging system 52 to produce a narrow sweeping beam of ultrasound directed from the piezoelectric elements of detector array 44 into the tissue of the breast. Echoes produced within the breast are then received by the acoustic sensors in detector array 44 and delivered to an ultrasound receiver 56, and then relayed to the ultrasound imaging system 52 using conventional ultrasound imaging techniques. As a result, an ultrasound image of the tissue may be created and presented on display 50 overlaid with or as a substitute for comparison to the TACT-generated image produced by the TACT system 48. Combined ultrasound and TACT imaging created in this manner may serve diagnostic purposes that cannot be realized by either modality alone, by permitting discrimination of tissue structures that are more readily recognized with each modality, and permitting direct comparison of images produced by each modality by a clinician operating the scanning system and viewing display 50.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. An imaging system for imaging structures of tissue, comprising:
    a detector array;
    an acoustic receiver coupled to said detector array for receiving acoustic signals generated in response to radiant energy delivered to said tissue and detected by said detector array,
    an image reconstructor coupled to said acoustic receiver for performing a backprojection algorithm to generate a representation of acoustic signals generated at points within the tissue, the representation for a point being based upon signals from plural detectors in said detector array;
    an ultrasound receiver coupled to said detector array for receiving echoes from an ultrasonic beam delivered into said tissue; and
    an ultrasound beam steering circuit coupled to said detector array for causing said array to generate said ultrasonic beam.

2. The imaging system of claim 1 further comprising a TACT processing system incorporating said image reconstructor for producing TACT images using acoustic signals detected by the said detector array, said TACT receiver coupled to said TACT processing system.

3. The imaging system of claim 1 further comprising an ultrasound imaging system, said ultrasound receiver coupled to said ultrasound imaging system.

4. The imaging system of claim 1 wherein said ultrasound beam steering circuit is coupled to and controlled by an ultrasound imaging system.

5. The imaging system of claim 2, wherein said TACT processing system sends images to a display.

6. The imaging system of claim 3, wherein said ultrasound imaging system sends images to a display.

7. A method for using an imaging system for imaging structures of tissue, comprising:
    coupling a transducer array to said tissue;
    receiving, with said transducer array, thermoacoustically acoustic signals originated within said tissue in response to radiant energy delivered to said tissue;
    performing a backprojection algorithm to generate a representation of acoustic signals generated at points within the tissue, the representation for a point being generated from signals from plural transducers in said transducer array;
    delivering a steered beam of ultrasound into said tissue;
    receiving echoes of said ultrasound beam with said transducer array and an ultrasound receiver; and generating an image of said tissue from one or both of said thermoacoustically generated signals and said echoes of said ultrasound beam.

8. The method of claim 7, wherein an image of the tissue is created from said echoes and an image of the tissue is created from said representation generated from said thermoacoustically generated signals, and said images are presented on display overlaid in spacial registration or in comparison with each other.

9. The method of claim 7, wherein said thermoacoustically generated signals are delivered to a TACT processing system for producing TACT images using acoustic signals detected by the said detector array.

10. The method of claim 7, wherein said ultrasound echoes are sent to an ultrasound imaging system.

11. The method of claim 7, wherein said ultrasound beam is generated using steering delays controlled by an ultrasound imaging system.

12. The method of claim 9, wherein said TACT processing system sends images to a display.

13. The method of claim 10, wherein said ultrasound imaging system sends images to a display.

* * * * *